(12) United States Patent
Kopp et al.

(10) Patent No.: US 8,378,836 B2
(45) Date of Patent: Feb. 19, 2013

(54) MAGNETIC FIELD STRENGTH THRESHOLD ALARM

(75) Inventors: Keith Kopp, Jensen Beach, FL (US); Harold Duane DeMent, Stuart, FL (US)

(73) Assignee: Kopp Development Inc., Jensen Beach, FL (US)

(*) Notice: Subject to any disclaimer, the term of this patent is extended or adjusted under 35 U.S.C. 154(b) by 601 days.

(21) Appl. No.: 12/623,616

(22) Filed: Nov. 23, 2009

(65) Prior Publication Data
US 2011/0121986 A1   May 26, 2011

(51) Int. Cl.
  *G01R 33/02* (2006.01)
  *G08B 21/02* (2006.01)
  *H01F 7/02* (2006.01)
(52) U.S. Cl. ........ 340/657; 324/259; 324/260; 335/234; 335/238; 340/551; 600/409
(58) Field of Classification Search .......... 324/301–302, 324/318–321, 244, 259–261; 335/220, 229, 335/234, 238, 296–306; 340/540, 551, 561, 340/624–625, 657, 572.1–572.6; 600/407, 600/409–410
See application file for complete search history.

(56) References Cited

U.S. PATENT DOCUMENTS

| | | | | |
|---|---|---|---|---|
| 2,629,792 A * | 2/1953 | Fitch | 335/281 |
| 2,898,422 A * | 8/1959 | Peek, Jr. | 335/83 |
| 2,934,621 A * | 4/1960 | Stewart | 335/95 |
| 3,229,063 A * | 1/1966 | Sakatos | 335/154 |
| 4,335,611 A * | 6/1982 | Bennett et al. | 73/514.19 |
| 4,634,969 A * | 1/1987 | Edlin et al. | 324/95 |
| 4,910,633 A * | 3/1990 | Quinn | 361/144 |
| 5,144,977 A * | 9/1992 | Eggerton et al. | 137/554 |
| 5,201,128 A * | 4/1993 | Olivier et al. | 33/355 R |
| 5,560,115 A * | 10/1996 | Fowler | 33/361 |
| 6,087,824 A * | 7/2000 | Shiao | 324/67 |
| 6,169,402 B1 * | 1/2001 | Oka et al. | 324/318 |
| 6,366,073 B1 * | 4/2002 | Shiao | 324/67 |
| 7,038,449 B1 * | 5/2006 | Wilson et al. | 324/259 |
| 2001/0030610 A1* | 10/2001 | Rochelle et al. | 340/686.6 |
| 2003/0171669 A1* | 9/2003 | Kopp | 600/410 |
| 2007/0132581 A1* | 6/2007 | Molyneaux et al. | 340/551 |
| 2007/0239231 A1* | 10/2007 | Ginggen | 607/63 |
| 2007/0282378 A1* | 12/2007 | Huang et al. | 607/2 |
| 2008/0290864 A1* | 11/2008 | Latraverse | 324/229 |
| 2009/0251316 A1* | 10/2009 | Mamourian et al. | 340/540 |
| 2009/0322325 A1* | 12/2009 | Ausserlechner | 324/260 |
| 2010/0199506 A1* | 8/2010 | Moureaux et al. | 33/361 |

* cited by examiner

*Primary Examiner* — Benjamin C Lee
*Assistant Examiner* — Stephen Burgdorf
(74) *Attorney, Agent, or Firm* — Cooper Legal Group, LLC

(57) ABSTRACT

A magnetic field strength threshold alarm that includes sensing means responsive to a magnetic field and actuating in response to field strength above a predetermined threshold, the sensing means being configured to be operational and able to actuate without consumption of energy; and alarm means for outputting an alarm responsive to the sensing means actuation, the alarm means being configured not to consume energy prior to actuation of the sensing means and only consuming energy subsequent to actuation of the sensing means. So, energy is not consumed by the alarm means prior to actuation. The alarm may be considered to include energy storage means for providing electrical energy, wherein the sensing means, the alarm means and energy storage means being operatively connected such that the electrical energy from the energy storage means is provided only when the sensing means is actuated.

12 Claims, 10 Drawing Sheets

MAGNETIC FIELD STRENGTH THRESHOLD ALARM

FIELD OF THE INVENTION

The present invention is in the field of devices or apparatus for detecting magnetic strength in the vicinity of an operating magnetic resonance imager (MRI) and responding when a preset magnetic field strength is exceeded.

BACKGROUND OF THE INVENTION

The MRI has become an invaluable tool for imaging and exploring the internal anatomy without surgery. MRI has the ability to distinguish healthy from diseased tissue, fat and muscle and adjacent structures within the body which other modalities cannot differentiate. MRI uses safe radio waves and a strong magnetic field to generate the information, which is processed by a computer, to create an image. There are now about 10,000 MRI machines currently in use in the United States.

Because of the desire for higher quality and higher resolution, the static magnetic field strength has increased steadily over the last 25 years, from a fraction of a Tesla to the current situation where 3 Tesla magnets are common and 7 Tesla magnets are now appearing on the market. Most new magnets for MRI are superconducting and as a result very expensive to start up, causing the requirement for the magnet to be kept always on. In an emergency, these superconducting MRI magnets cannot be turned off quickly.

The strong magnetic field associated with the area near to the MRI presents a danger of ferromagnetic objects being attracted to the strong magnetic field. There are numerous recorded incidents of objects becoming flying projectiles resulting in injury to the nearby personnel or the patient. Costly damage may be caused to the MRI machine itself from the impact of the projectile.

In order to reduce the risk of a ferromagnetic projectile accident, a ferromagnetic detection system as described in U.S. Pat. No. 7,489,128 MRI PROTECTOR is employed at the entrance of the room containing the MRI machine. This device will provide an alarm should a device containing ferromagnetic material pass through the ferromagnetic detector portal.

It is sometimes necessary to bring devices which contain ferromagnetic material into the room containing the MRI machine. As a result, ferromagnetic detectors do not prove useful in this situation other than to alert personnel that a potential risk may be present. Medical equipment, such as infusion pumps, contrast injectors, patient monitors as well as anesthesia machines, is commonly necessary in the room containing the MRI machine.

In addition to the potential projectile risk posed by medical equipment brought into the magnetic field of the MRI, many medical devices do not function correctly or are damaged when operated in high magnetic fields. A contrast injector, for example, may inject an incorrect quantity of contrast agent when the device is exposed to a magnetic field greater than its design magnetic field maximum value.

A variety of medical devices can operate safely in the vicinity of the MRI magnet if precautions are made to insure that the medical device is kept in an area where the magnetic field strength is below the limit where the device will perform correctly and/or will not present a ferromagnetic projectile risk. Medical equipment brought into the MRI room is quite commonly on carts with caster wheels. The equipment may, therefore, be easily moved or accidently bumped into an area where the magnetic field is dangerously high. Rarely are there markings indicating the various magnetic field strengths on the floor or elsewhere. As a result, the personnel may not be aware of the present danger. What is needed is a device to alert the personnel of the dangerous magnetic field in which the medical device is immersed.

The electromagnetic signal produced during MRI and used to create the image is very weak. For this reason, modern MRIs are contained in a specially constructed electromagnetically shielded room, sometimes called the screen room or MRI room. Any piece of electrical or electronic equipment operating inside this screen room can be a potential source of interference. Electromagnetic interference can cause a degradation of the diagnostic quality of the image produced by the MRI process. As a consequence, electrical equipment is not brought into the screen room unless absolutely necessary and only then after a rigorous testing process to validate that the device does not degrade the performance of the MRI. Even after this validation process, there is still a significant risk that the MRI image quality may be compromised.

Equipment such as patient monitors, infusion pumps and power injectors are moved frequently within the screen room. As such, a power cord supplying electricity to the equipment is inconvenient as well as being a potential risk of electromagnetic interference. Because of this, most electrical equipment brought into the MRI screen room is battery operated.

A variety of gaussmeters are on the market utilizing various sensing techniques including Hall Effect, flux gate and anisotropic magneto-resistive. Magnetic field strength alarms are known for detecting the magnetic field strength in the MRI environment. For example U.S. Pat. No. 4,954,812 entitled MAGNETIC FIELD ALARM INDICATOR discloses a magnetic field alarm detector comprised of a plurality of magnetic field detectors mounted in a horizontal plane for detecting respective rotational components of a magnetic field. To achieve an even moderately uniform sensitivity in a 360 degree field of view, at least 3 sensors must be used. More sensors are needed for better rotational sensitivity uniformity. The Hall Effect sensors used as well as the necessary processing electronics use a significant amount of electrical power. To be effective, the invention disclosed consumes power anytime the device described is monitoring the magnetic field strength. As a consequence, the batteries must be charged or replaced regularly. Further, since the disclosed invention must be powered at all times while the device is in the screen room, there is a significant risk of the device causing electromagnetic interference. This risk is increased if a number of pieces of medical equipment in the screen room are fitted with the alarm described in the invention.

U.S. Patent Application No. 2007/0132581 entitled METHOD AND APPARATUS FOR FERROUS OBJECT AND/OR MAGNETIC FIELD DETECTION FOR MRI SAFETY The device described attempts to address the power consumption issue by using an radio-frequency identification (RFID) system to turn the device on when it enters the MRI room and off again when it leaves the MRI room. This approach has potential of lowering the power consumption of the device under certain circumstances. However, the types of medical equipment described above are quite commonly stored in the MRI room. As a result, there is no power consumption reduction in this common situation since the device must be left powered. Further, the risk of electromagnetic interference with the MRI machine is still present since the device is powered while it is in the MRI room. The risk of electromagnetic interference may actually be increased by the presence of RFID circuitry.

BRIEF SUMMARY OF INVENTION

The following summary presents a simplified summary in order to provide a basic understanding of some aspects of the systems and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the more detailed description that is presented later.

In accordance with one aspect, the present invention provides a magnetic field strength threshold alarm that includes sensing means responsive to a magnetic field and actuating in response to field strength above a predetermined threshold, the sensing means being configured to be operational and able to actuate without consumption of energy; and alarm means for outputting an alarm responsive to the sensing means actuation, the alarm means being configured not to consume energy prior to actuation of the sensing means and only consuming energy subsequent to actuation of the sensing means.

In accordance with another aspect, the present invention provides a magnetic field strength threshold alarm that includes sensing means responsive to a magnetic field and actuating in response to field strength above a predetermined threshold, alarm means for outputting an alarm responsive to the sensing means actuation, and energy storage means for providing electrical energy for at least the alarm means to output the alarm, wherein the sensing means, the alarm means and energy storage means being operatively connected such that the electrical energy from the energy storage means is provided only when the sensing means is actuated.

In accordance with yet another aspect, the present invention provides a magnetic field strength threshold alarm that includes sensing means responsive to a magnetic field and actuating in response to field strength above a predetermined threshold, the sensing means being configured to be operational and able to actuate without consumption of energy, alarm means for outputting an alarm responsive to the sensing means actuation, and energy storage means for providing electrical energy for at least the alarm means to output the alarm, wherein the alarm means being configured and operatively connected to the energy storage means such that energy is not consumed by the alarm means prior to actuation of the sensing means.

BRIEF DESCRIPTION OF THE DRAWINGS

The foregoing and other aspects of the invention will become apparent to those skilled in the art to which the invention relates upon reading the following description with reference to the accompanying drawings, in which.

DETAILED DESCRIPTION OF EXAMPLE EMBODIMENTS

Figure 1A:
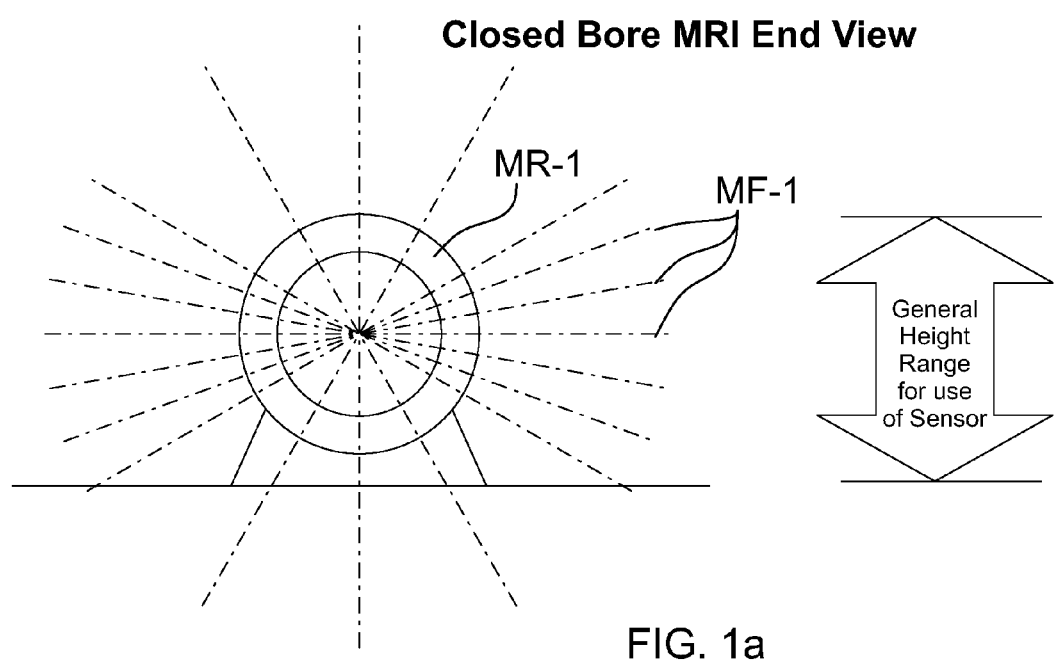
FIG. 1a is a schematic end view of a static magnetic field diagram of a closed bore magnetic resonance imager (MRI)

Example embodiments that incorporate one or more aspects of the invention are described and illustrated in the drawings. These illustrated examples are not intended to be a limitation on the invention. For example, one or more aspects of the invention can be utilized in other embodiments and even other types of devices. Moreover, certain terminology is used herein for convenience only and is not to be taken as a limitation on the invention.

Figure 1B:
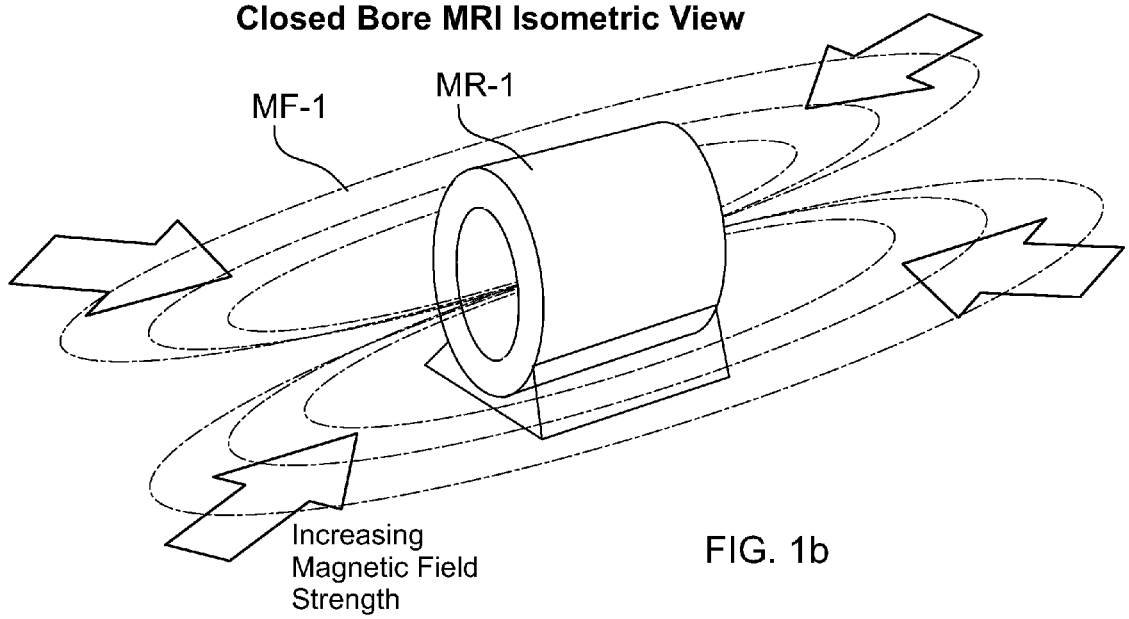
FIG. 1b is a schematic perspective view of a static magnetic field diagram of a closed bore MRI.

A schematic example of a closed bore magnetic resonance imager (MRI) is shown within FIGS. 1a and 1b. It can be seen that that the magnetic field MF-1 surrounding the MRI magnet MR-1 is substantially horizontal. In accordance with one aspect of the present invention, in order to efficiently sense such a magnetic field a sensor could rely on a relationship that the torque on a magnet is the vector cross product of the magnetic dipole moment of the magnet and the external magnetic field.

Figure 3:
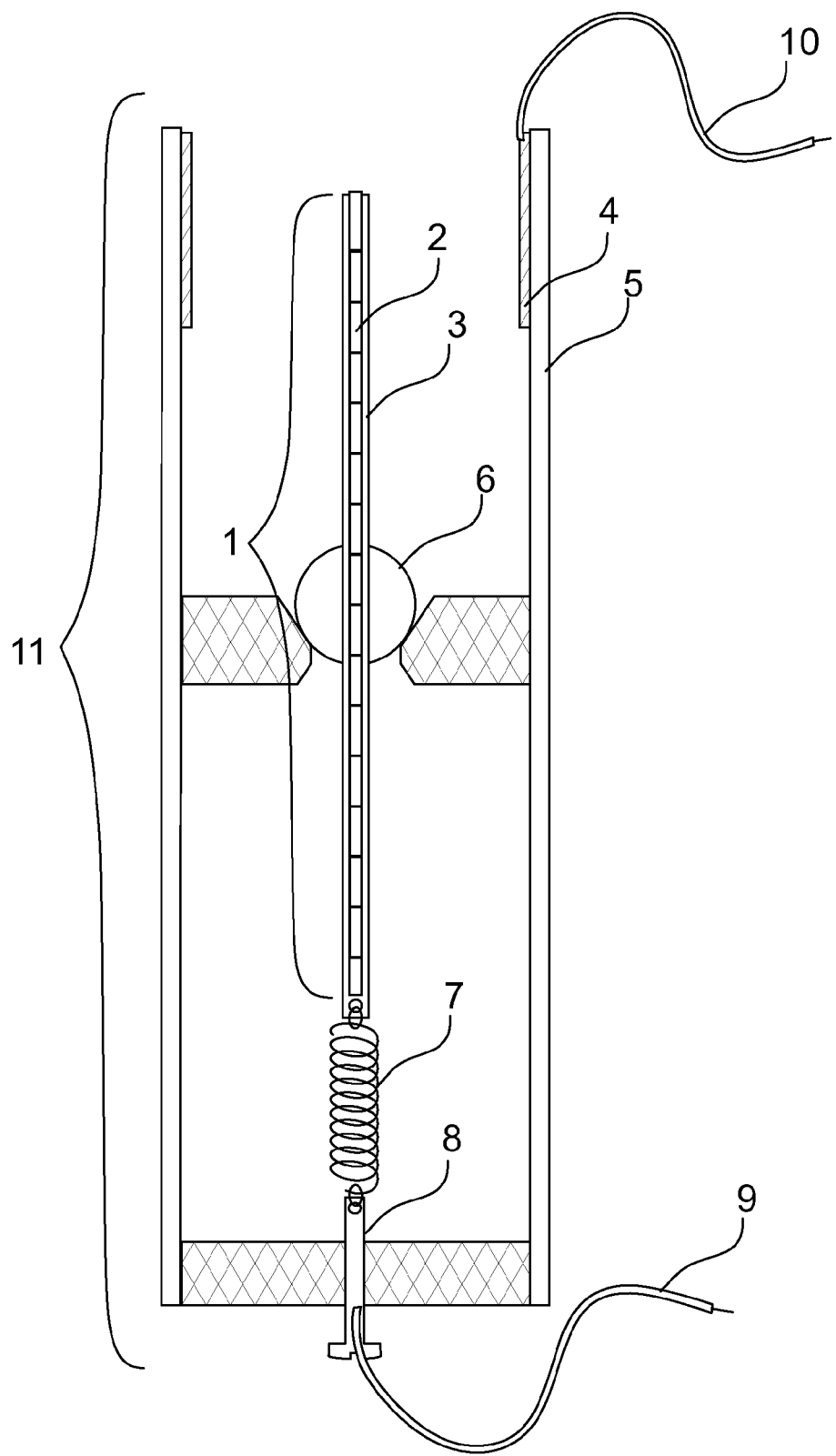
FIG. 3 is a schematic view of Magnetic field strength sensor with no external field applied.

Turning to FIG. 3 an example of a magnetic field strength sensor 11 in accordance with an example aspect of the present invention for sensing the magnetic field of FIGS. 1a and 1b is shown. The field strength sensor 11 includes a sensor magnet 1 (shown in a neutral position within FIG. 3) located within a cylindrical housing 5. The sensor magnet 1 may be provided as a number of smaller cylindrical magnets 2 contained in an electrically conductive tube 3. The number of the small cylindrical magnets 2 can be changed to change the magnetic dipole moment of the sensor magnet 1.

The sensor magnet 1 is pivotally supported by a spherical ball bearing 6, which in turn is supported upon a rotational/pivot seat that is in turn supported/fixed within the cylindrical housing 5. The ball bearing 6 is a low frictional resistance electrical insulator, such as polytetrafluoroethylene (PTFE). Within the shown example the ball bearing 6 supports the sensor magnet 1 at approximately the middle of the sensor magnet.

A bias spring 7 is attached to a bottom of the sensor magnet 1. The spring 7 provides a biasing force that urges the sensor magnet 1 back to the neutral position shown within FIG. 3. Such a spring biasing force would be in opposition to force applied to the sensor magnet 1 by the external magnetic field from the MRI shown within FIGS. 1a and 1b. The spring 7 (FIG. 3) can be made from beryllium copper so as not to interact with the magnetic field. Since the spring 7 is on the axis of deflection of the sensor magnet 1, the balancing force for a given angle of the deflection of the sensor magnet 1 is the same without regard to the direction of deflection. Thus, the strength of the magnetic field required to close the switch is the same anywhere in the 360 field of view of the magnetic field strength sensor 11.

In turn the spring 7 is connected to an adjustment screw 8. The adjustment screw 8 may be rotated to change the tension within the spring 7. It is to be appreciated that the field strength sensor 11 is adjustable to adjust sensitivity. Specifically, changing the number of small cylindrical magnets 2 within the sensor magnet 1 can be used to as a coarse adjustment of the magnetic field strength trip point of the sensor. Fine adjustment of the magnetic field strength trip is accomplished by spring adjustment screw 8.

A contact ring 4 is located within the housing 5 at a location at which an upper end of the electrically conductive tube 3 of the sensor magnet 1 may move into contact with the contact ring. A conductive wire 9 is attached to the threshold adjust screw 8 and a wire 10 is attached to the contact ring 4. When the sensor magnet 1 pivots under the influence of the magnetic force from the MRI and the magnetic influence is sufficiently strong to overcome the bias force of the spring 7, the upper end of the conductive tube 3 contacts the contact ring. Thus, there is electrical connection between the wire, the adjustment screw 8, the conductive tube 3, the contact ring 4, and the wire 10. As such, the electrically connected components create a closed switch. Such a switching action can provide an indication usable as a signal. Also, the amount of magnetic force needed to displace the spring-biased sensor magnet 1 can be selected based upon adjustment. As such the switching action is also indicative of field strength.

Figure 4A:
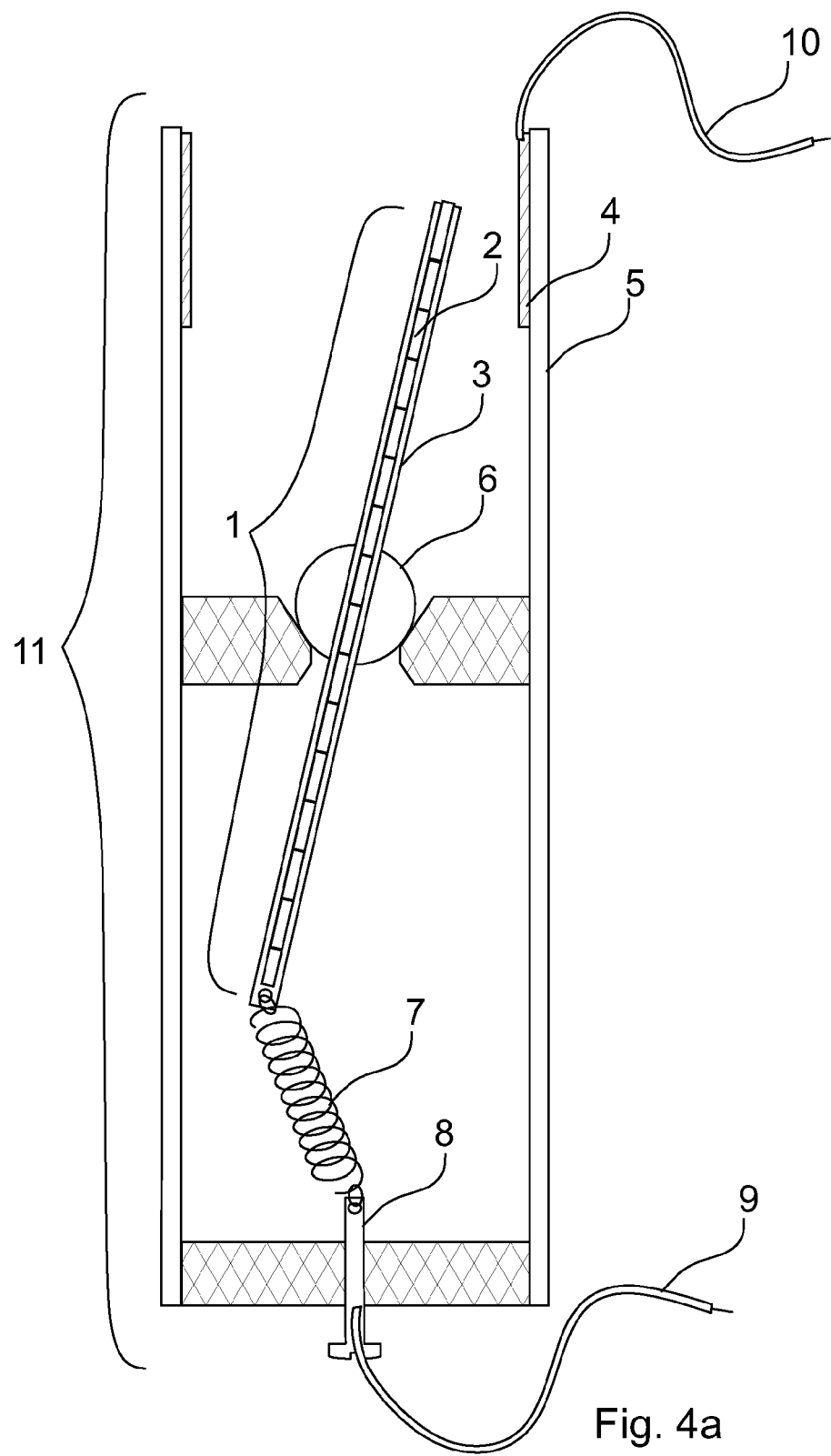
FIG. 4a is a view of the Magnetic field strength sensor of FIG. 3, but with a Below Threshold external magnetic field applied.
Figure 4B:
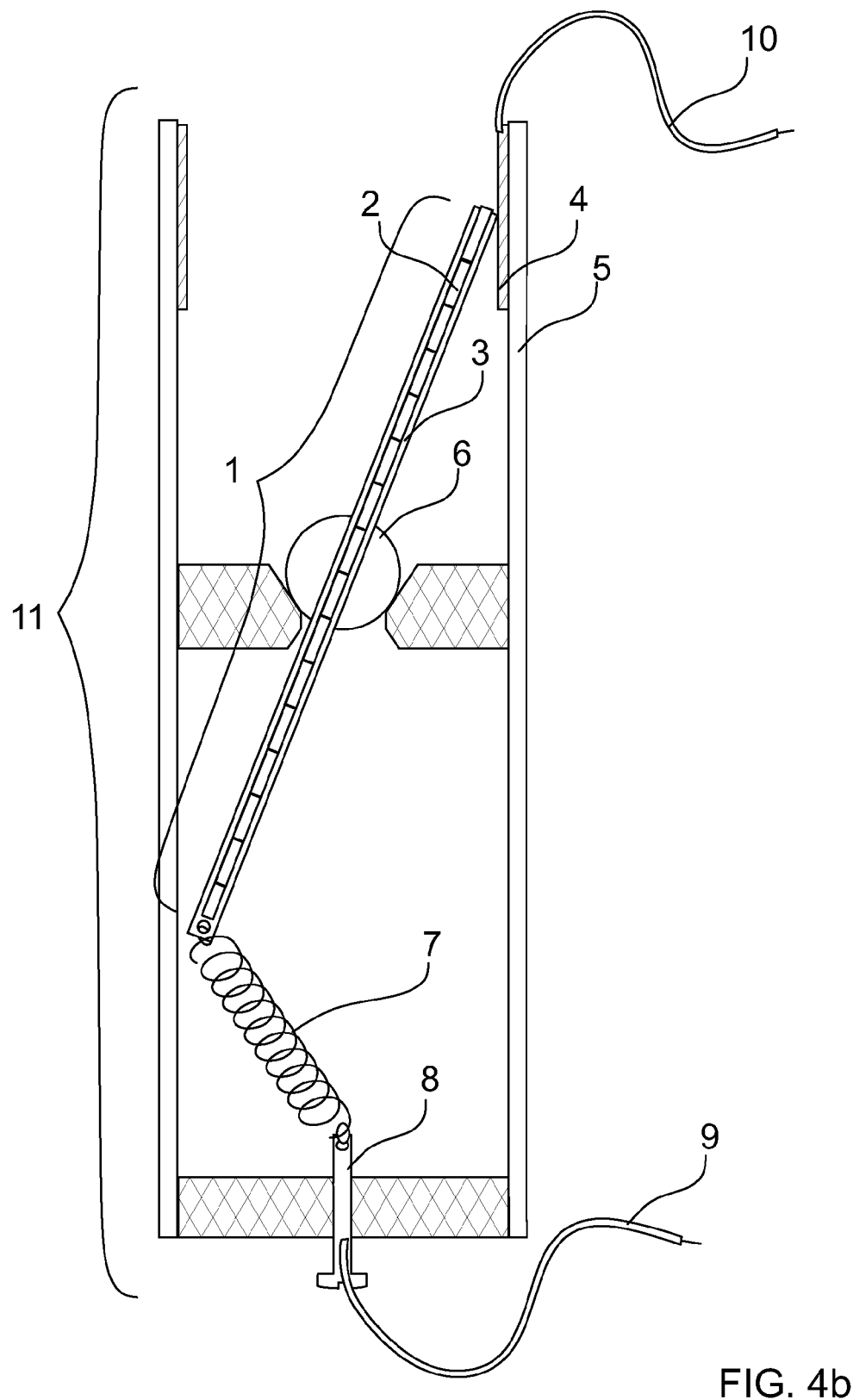
FIG. 4b is a view of the Magnetic field strength sensor of FIG. 3, but with an Above Threshold external magnetic field applied.

The sensor magnet 1 experiences the maximum torque with the sensor magnet 1 oriented vertically when the field strength sensor 11 is exposed to the substantially horizontal magnetic field shown FIG. 1. Specifically, when the sensor magnet 1 in the Magnetic Field Strength Sensor 11 shown in FIG. 3 is brought near the MRI magnet MR-1 shown in FIG. 1, the sensor magnet 1 will experience a torque such that the sensor magnet 1 will attempt to orient along the magnetic field lines MF-1 of the MRI magnet MR-1 shown in FIG. 1. In FIG. 4a the rotation resulting from the torque on the sensor magnet 1 is restricted by the force of the spring 7. FIG. 4b shows the situation when the field strength sensor 11 is brought sufficiently close to the MRI magnet MR-1 such that the sensor magnet 1, deflects to the degree necessary to bring the sensor magnet 1 in contact with the cylindrical electrical contact ring 4. Of course it is to be appreciated that the field strength sensor may have variation of its configuration. As such, field strength sensor 11 is one example of sensing means responsive to a magnetic field and actuating in response to field strength above a predetermined threshold. It is to be appreciated that other examples of sensing means are contemplated.

Figure 5:
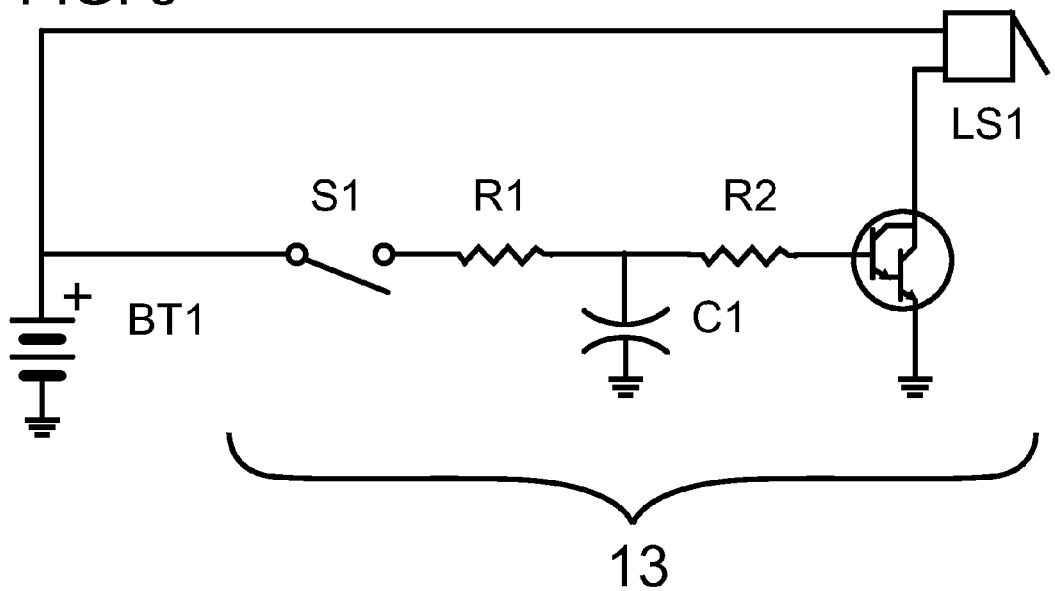
FIG. 5 is a schematic circuit diagram of an example alarm activation circuit.

Referring to FIG. 5, an example activation circuit 13 is shown. The activation circuit 13 is operatively connected to the field strength sensor 11 and an alarm device LS1, and is a normally open circuit that is responsive to become a closed circuit upon sensing a magnetic field strength above a certain, predetermined threshold. Within FIG. 5, the field strength sensor 11 is schematically represented by S1 because the field strength sensor acts as a switch. A battery BT1 is connected in parallel to the field strength sensor (as a switch) S1 and the alarm device LS1. The alarm device LS1 is operatively connected through a transistor (e.g., Darlington) Q1 of the activation circuit 13 to ground. The field strength sensor (as a switch) S1 is connected through a series of resistors R1 and R2 of the activation circuit 13 to a control base of the transistor Q1, with a capacitor C1 of the activation circuit 13 connected between a node interposed between the resistors and ground. Resistor R1 and capacitor C1 form a low pass filter to prevent transient events from activating the alarm device. Resistor R2 limits the current supplied to the Darlington transistor Q1. As such, the field strength sensor (as a switch) S1 controls operation of the transistor Q1. Accordingly, the field strength sensor (as a switch) S1 controls operation (i.e., ON-OFF) of the alarm device LS1. Of course, it is to be appreciated that the example activation circuit 13 is just one example and is not specific limitation upon the present invention since the activation circuit could be configured differently as will be appreciated by the person of ordinary skill in the art.

When the magnetic field strength sensor S1 is open, meaning the magnetic field strength at the sensor S1 is below the trip threshold, transistor Q1 is turned off and no current flows through the alarm device LS1. Therefore there is no electrical energy being drawn from the battery BT1 when the magnetic field strength at the sensor S1 is below the trip point.

When the magnetic field strength sensor S1 is exposed to a magnetic field strength above the predetermined trip threshold the sensor S1 closes. With the field strength sensor S1 closed, transistor Q1 is turned ON and current flows through the alarm device LS1. Also, the capacitor C1 becomes charged. When the magnetic field strength sensor S1 is moved away from the MRI magnet, the magnetic field strength will fall below the predetermined trip point, causing the magnetic field strength switch S1 to open. Since the capacitor C1 is charged, current will be supplied to transistor Q1, keeping it turned ON for a period of time dependant on the value of capacitor C1 and resistor R2. While transistor Q1 is still turned on, the alarm device will remain on. This latching function of R2 and C1 keeps short term switch S1 open periods, caused by vibration etc., from deactivating the alarm device LS1.

With regard to the alarm device LS1, the alarm may have any of a variety of forms/configurations including audio and/or visual output. The output of Q1 may be used as an input to, for example, a patient monitor to which the present invention is attached. In this case, the display and/or the alarm of the patient monitor are used as a status indicator for the magnetic field strength level from the magnetic field strength sensor S1. The output from Q1 may also be used to activate additional safety device(s). For Example, the output from Q1 could be connected to a solenoid which, in turn, locks the wheels on the monitored cart should the cart be brought into an area considered to be a danger zone of the MRI environment. The locked wheels should discourage further movement of the cart into the danger zone of the MRI environment.

As such, alarm device LS1 is one example of alarm means for outputting an alarm responsive to the sensing means actuation. It is to be appreciated that other examples of alarm means are contemplated. Battery BT1 is one example of energy storage means for providing electrical energy for at least the alarm means to output the alarm. It is to be appreciated that other examples of energy storage means are contemplated. The activation circuit 13 is one example of control means for operative connection of the sensing means, the alarm means and energy storage means and for controlling provision of electrical energy such that the electrical energy is provided only when the sensing means is actuated. It is to be appreciated that other examples of control means are contemplated.

is to be appreciated that the alarm means is configured not to consume energy prior to actuation of the sensing means and only consuming energy subsequent to actuation of the sensing means. Also it is to be appreciated that the alarm means and energy storage means are operatively connected such that the electrical energy from the energy storage means is provided only when the sensing means is actuated. Also it is to be appreciated that the alarm means is configured and operatively connected to the energy storage means such that energy is not consumed by the alarm means prior to actuation of the sensing means.

shows a first example embodiment device GA1 that has at least one aspect in accordance with the present invention within an equipment mountable enclosure ME-1. With the shown example, the magnetic field strength sensor 11, the activation circuit 13, the alarm device LS1 (which is identified within the example as audio and visual alarms 14) and the battery BT1 (which is identified within the example as UltraLife battery 12) are located within the equipment mountable enclosure ME-1. In the example, the UltraLife battery 12 is provided as a commonly available 9V battery configuration, but is a special UltraLife lithium manganese dioxide type with a 10 year service life. The use of this battery will require no replacement for up to 10 years since no power is consumed in the normal operating condition. Because of long normal operation battery life, recharging capability or RFID activation of the device are unnecessary. However, such a configuration may differ. Even when no power is being consumed, the device GA1 is capable of producing an alarm without need for turning on a power switch or other means of activation. Therefore the device GA1 can remain active and attached to medical equipment left in the MRI room for an extended period of time with no loss of battery 12 energy level or service life.

previously discussed, the MRI imaging process is extremely sensitive to degradation by electromagnetic interference. Any electrical device brought into the MRI screen room can pose a risk of interference. In the prior art referenced, special shielding and component selection of the devices brought into the MRI screen room are used to reduce the risk of electromagnetic interference. The measures taken by the prior art reduce but do not eliminate the risk of electromagnetic interference. The present invention totally eliminates the possibility of electromagnetic interference during normal operation of the present invention. This is accomplished by removing all electric current from the present invention in the non-alarming condition. A time changing magnitude electrical current is necessary to generate electromagnetic radiation. Without a time changing magnitude electrical current or indeed any electrical current at all, there is no possibility of the present invention causing electromagnetic interference to the MRI imaging process.

Battery 12, as well as all the other components used, have a very low ferromagnetic content. Low ferromagnetic content of the device GA-1 ensures the product itself does not present a ferromagnetic projectile risk.

Since the magnetic field strength sensor 11 has a 360 degree field of view with uniform magnetic field sensitivity, the device GA-1 will activate the alarm irrespective of the rotation of the piece of medical equipment to which it attached. In the prior art discussed, at least 3 sensors were need to achieve a limited uniformity of magnetic field strength sensitivity over a 360 degree field of view.

Figure 2A:
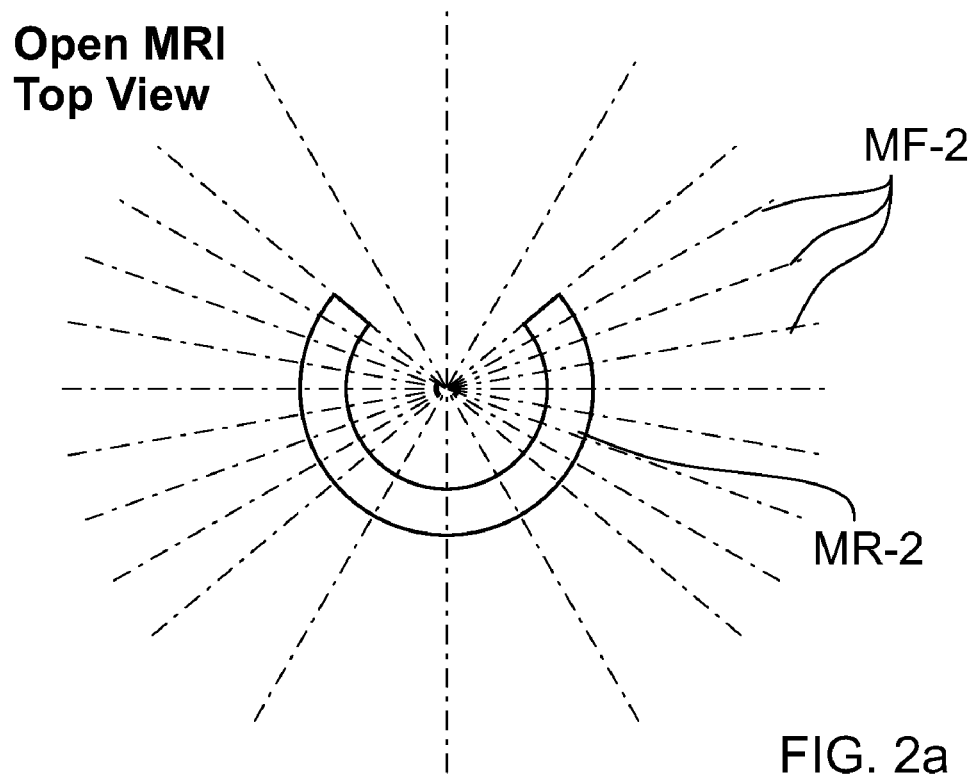
FIG. 2a is a schematic top view of a static magnetic field diagram of an open bore MRI.
Figure 2B:
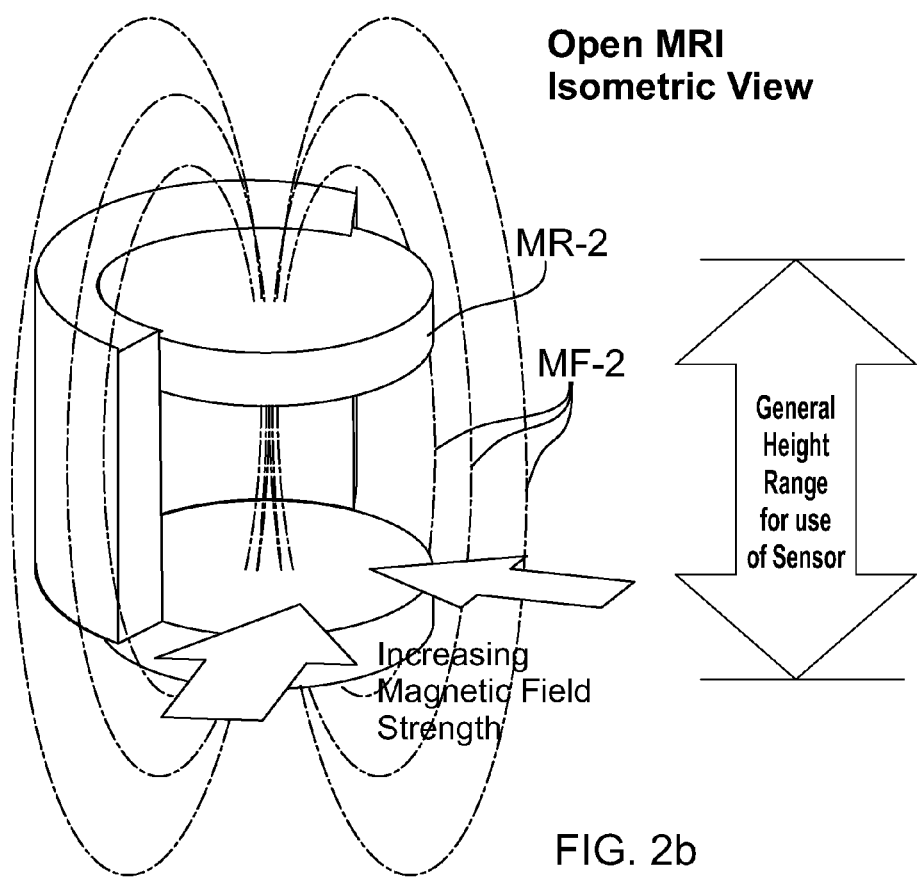
FIG. 2b is a schematic isometric view of a static magnetic field diagram of an open bore MRI.

Turning to FIGS. 2a and 2b, an example of an open MRI machine and associated magnetic field lines are shown. The magnetic field lines MF-2 are substantially vertical in orientation. In accordance with an aspect of the present invention, one or more embodiments will function effectively in this environment if the device is rotated 90 degrees such that the sensor magnet 1 (FIG. 3) is horizontal with no external magnetic field applied. For such an embodiment (i.e., horizontally oriented) the ball bearing 6 is located at the center of mass of the sensor magnet 1 to remove any torque component caused by gravity. Locating the ball bearing 6 at the center of mass of the magnet also eliminates any torque moment on the sensor magnet 1 from the acceleration of the medical device to which the present invention is attached.

Another embodiment in accordance with an aspect of the present invention can include 2 sensors configured such that one sensor is vertically oriented, the other is horizontally oriented. This configuration would allow ready use for either the closed bore MRI MR-1 shown in FIGS. 1a and 1b and the open bore MRI MR-2 shown in FIGS. 2a and 2b without the need for the device to be rotated 90 degrees when moved from one type of MRI device to the other.

Figure 7:
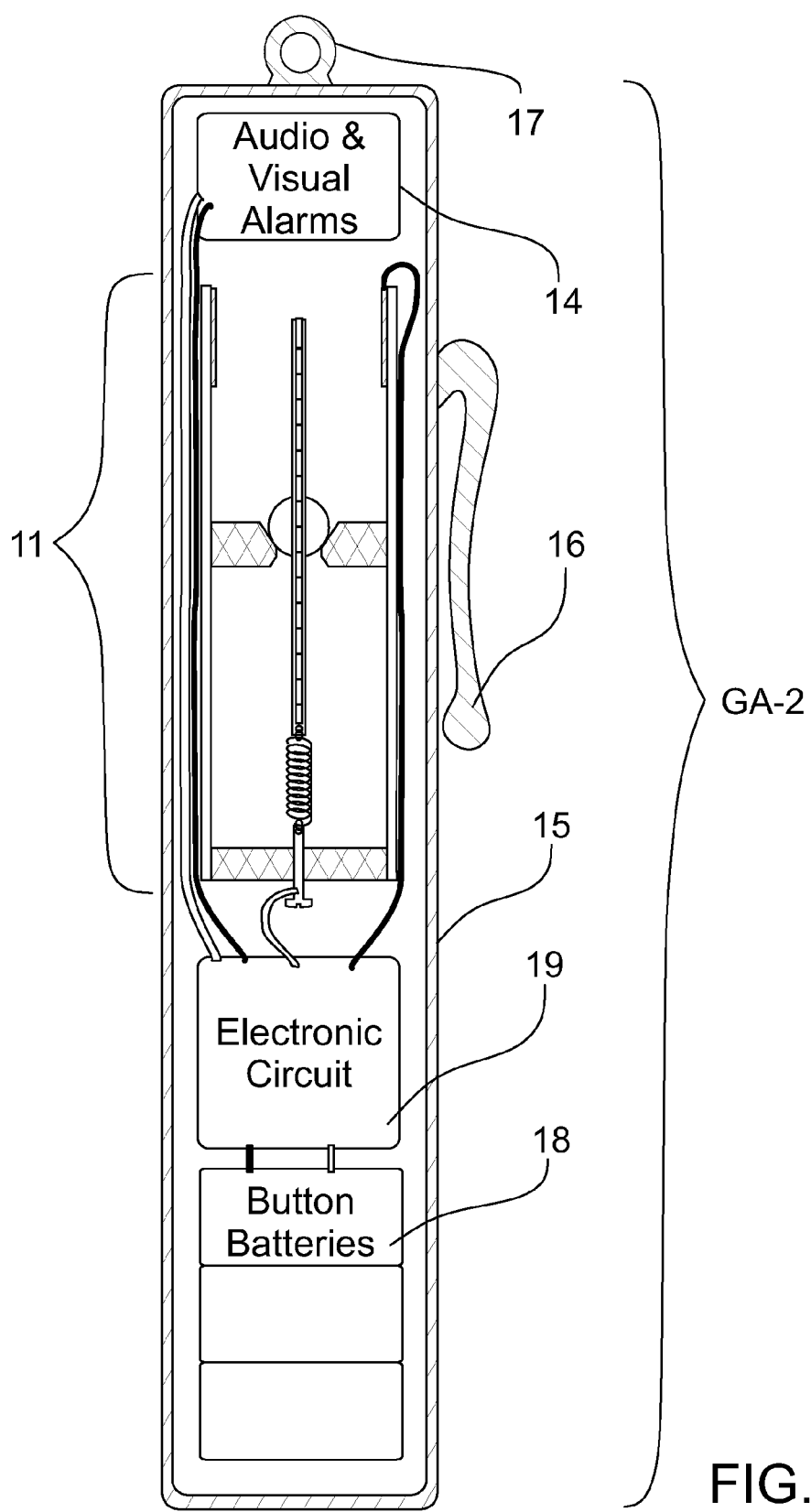
FIG. 7 is a schematized diagram of an example of a wearable alarm device.

FIG. 7 shows another embodiment of a device GA-2 in accordance with an aspect of the present invention. This device GA-2 to be worn by personnel working or otherwise exposed to the strong magnetic field of the MRI environment. This embodiment will alert the wearer and nearby personnel that wearer has entered an area of excessive magnetic strength. Numerous medical regulations as well as international safety standards limit the general public to magnetic field strengths of less than 5 gauss. The risk of exposure to excessive magnetic field strength for personnel with cardiac pacemakers, medical implants or who are pregnant is even greater.

Figure 6:
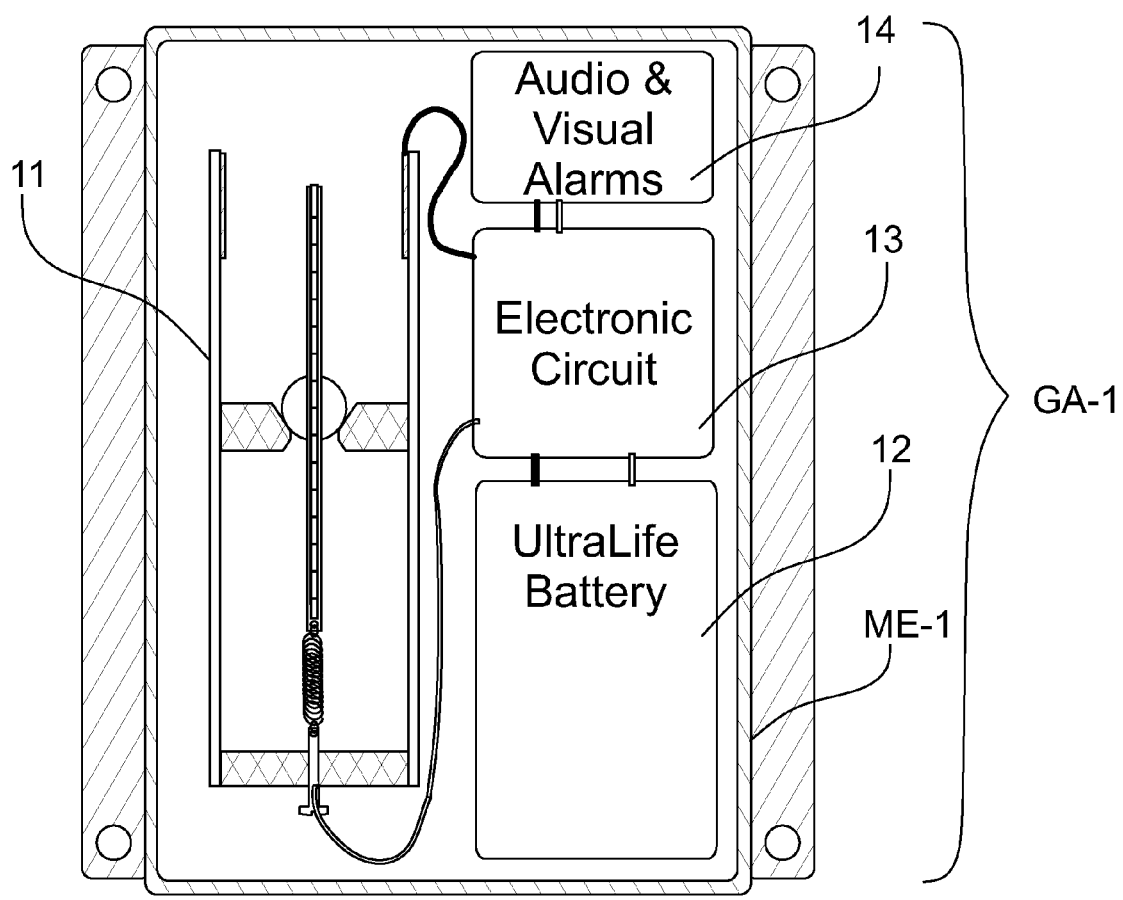
FIG. 6 is a schematized diagram of an example equipment mountable alarm device.

The device GA-2 is contained in an enclosure 15 similar to a ballpoint pen. A pocket clip 16 orients the magnetic field strength sensor 11 vertically. Alternatively, a ring 17 located at a top of the enclosure allows the attachment of a lanyard to be worn around the neck. An activation circuit 19 is provided and the configuration may be identical or similar to the activation circuit 13 as shown in FIG. 5 and presented in FIG. 6. Batteries 18 (FIG. 7) are provided (i.e., providing the function of BT1 and shown in FIG. 5. The batteries 18 may be button type batteries, which have a small compact size. Similar to the other example, audio and visual alarms 14 are operatively connected to the magnetic field strength sensor 11, and the batteries 18 via the activation circuit 19. The locations, from bottom to top of the device GA-2, of the button batteries 18, activation circuit 19, magnetic field strength sensor 11 and audio and visual alarms 14 are shown. However, such locations may be varied.

In addition to the MRI environment, the present invention is also applicable to other nuclear magnetic resonance (NMR) devices, such as NMR spectrometers. Some of the NMR spectrometers have magnetic field strengths in excess of 20 Tesla.

As such, it is to be appreciated that the present invention may include any combination of the above-mentioned aspects. Some example aspects that the present invention provides include the following, which can be grouped together in any combination.

A magnetic field strength threshold alarm that includes sensing means responsive to a magnetic field and actuating in response to field strength above a predetermined threshold, the sensing means being configured to be operational and able to actuate without consumption of energy; and alarm means for outputting an alarm responsive to the sensing means actuation, the alarm means being configured not to consume energy prior to actuation of the sensing means and only consuming energy subsequent to actuation of the sensing means.

Alternatively, a magnetic field strength threshold alarm that includes sensing means responsive to a magnetic field and actuating in response to field strength above a predetermined threshold, alarm means for outputting an alarm responsive to the sensing means actuation, and energy storage means for providing electrical energy for at least the alarm means to output the alarm, wherein the sensing means, the alarm means and energy storage means being operatively connected such that the electrical energy from the energy storage means is provided only when the sensing means is actuated.

Alternatively, a magnetic field strength threshold alarm that includes sensing means responsive to a magnetic field and actuating in response to field strength above a predetermined threshold, the sensing means being configured to be operational and able to actuate without consumption of energy, alarm means for outputting an alarm responsive to the sensing means actuation, and energy storage means for providing electrical energy for at least the alarm means to output the alarm, wherein the alarm means being configured and operatively connected to the energy storage means such that energy is not consumed by the alarm means prior to actuation of the sensing means.

The magnetic field strength threshold alarm may further include control means for operative connection of the sensing means, the alarm means and energy storage means and for controlling provision of electrical energy such that the electrical energy is provided only when the sensing means is actuated.

The magnetic field strength threshold alarm may be configured such that no electromagnetic energy radiates from the magnetic field strength threshold alarm when the sensing means is not actuated.

The sensing means may be configured to be responsive to the magnetic field independent of direction of incidence of the magnetic field onto the sensing means.

The sensing means may include a switch operable between a switch-open condition and a switch-closed condition, and the switch changing from the switch-open condition to the switch-closed condition upon field strength exceeding the predetermined threshold.

The sensing means may include an adjustable spring to change the field strength threshold at which the switch changes from the switch-open condition to the switch-closed condition.

The sensing means may include at least one magnet, with the magnet number being related to change of the field strength threshold at which the switch changes from the switch-open condition to the switch-closed condition.

The sensing means may be configured such that the sensing means cannot be erroneously actuated by acceleration.

The sensing means may include a pivotable member that has a pivot point coincident with a center or mass.

The alarm means may include at least one of an audio alarm and a visual alarm.

The magnetic field strength threshold alarm may be configured such that the sensing means is responsive to a magnetic field from either an open bore MRI or a closed bore MRI.

The sensing means may include at least one magnetic field strength sensor that is responsive to a respective magnetic field from either an open bore MRI or a closed bore MRI.

The magnetic field strength threshold alarm may be configured such that the sensing means is responsive to a magnetic field from a nuclear magnetic resonance device.

The magnetic field strength threshold alarm may be configured to be attached to equipment that may be brought into an MRI magnet room, and which will provide an alert in response to field strength from an MRI within the MRI magnet room above the predetermined threshold at the location of the equipment.

The magnetic field strength threshold alarm may be configured to be worn by a person.

A magnetic field strength sensor which includes a magnetized bar which experiences torque in a magnetic field. As the magnetic field increases, the torque will eventually be sufficient to overcome the spring tension. The magnetized bar will the make contact with the side of a cylindrical contact area and close the electrical circuit. The threshold or "set point" of the magnetic field strength sensor can be controlled by adjusting the spring tension or changing the magnet used in the bar magnet to close the contact at a specific static magnetic field strength produced by an MRI magnet. When the preset magnetic field strength has been reached, the magnetic field strength sensor will close the electrical switch. The bar magnet is free to deflect in the entire 360 degree field of view. The closing of the switch will charge a capacitor from a battery. The energy stored in this capacitor will activate a circuit which will connect and latch the battery to an alarm circuit. The alarm will, in turn, generate an alarm to warn personnel that the equipment has entered an area that has a magnetic field strength greater than the preset magnetic field strength value. If the alarm is not active, no energy is drained from the battery and no electromagnetic energy is radiated.

The invention has been described with reference to the example embodiments described above. Modifications and alterations will occur to others upon a reading and understanding of this specification. Example embodiments incorporating one or more aspects of the invention are intended to include all such modifications and alterations insofar as they come within the scope of the appended claims.

What is claimed:

1. A magnetic field strength threshold alarm including:
   a sensor responsive to a magnetic field and actuating in response to a strength of the magnetic field above a predetermined threshold, the sensor including:
     a housing including a seat support and an electrical contact;
     a movable member supported by the support of the housing for movement through a 360° range of directions, the movable member including a magnet responsive to the magnetic field to cause movement of the movable member irrespective of direction of incidence of the magnetic field, the movable member and the magnet thereof being configured to be operational such that the magnet responds to the magnetic field to move the moveable member without consumption of energy, the movable member also including an electrical conductor, movement of the movable member responsive the magnetic field of strength above the predetermined threshold causes the electrical conductor of the movable member to electrically engage the electrical contact of the housing so that electrical energy may flow through the electrical conductor of the movable member; and
     a bias member is connected between the movable member and the housing to bias the movable member away from an engagement of the electrical conductor of the movable member to the electrical contact of the housing;
     wherein the movable member includes a single sphere as a pivot point, located coincident with a center of mass of the movable member, the single sphere supported by the housing seat support, and the bias member biases the single sphere into engagement with the seat support; and
   an alarm device operatively connected to the sensor and outputting an alarm, via consumption of electrical energy, responsive to the sensor actuation via receipt of electrical energy proceeding through the electrical conductor of the movable member and the electrical contact of the housing responsive the magnetic field of strength above the predetermined threshold, the sensor and alarm device being configured such that the alarm device is only powered via the sensor actuation so that the alarm device does not to consume energy without the sensor actuation.

2. The magnetic field strength threshold alarm as set forth in claim 1, further including a circuit, operatively connected to the sensor and the alarm device, and an energy storage device, operatively connected to the circuit, the circuit operates to provide electrical energy from the energy storage device to the alarm device only when the sensor is actuated.

3. The magnetic field strength threshold alarm as set forth in claim 1, wherein the magnetic field strength threshold alarm is configured such that no electromagnetic energy radiates from the magnetic field strength threshold alarm when the sensor is not actuated.

4. The magnetic field strength threshold alarm as set forth in claim 1, wherein the bias member includes an adjustable spring, and adjustment to the spring changes the predetermined threshold of the strength of the magnetic field above which the sensor actuates.

5. The magnetic field strength threshold alarm as set forth in claim 1, wherein the movable member includes one or more magnets, where the number of magnets changes the predetermined threshold of the strength of the magnetic field above which the sensor actuates.

6. The magnetic field strength threshold alarm as set forth in claim 1, wherein the sensor is configured such that the sensor cannot be erroneously actuated by acceleration.

7. The magnetic field strength threshold alarm as set forth in claim 1, wherein the movable member includes a plurality of magnets.

8. The magnetic field strength threshold alarm as set forth in claim 7, wherein at least one of the plurality of magnets being on one side of the pivot point and at least one other of the plurality of magnets being located on an opposite side of the pivot point.

9. The magnetic field strength threshold alarm as set forth in claim 1, wherein the alarm device includes at least one of an audio alarm and a visual alarm.

10. The magnetic field strength threshold alarm as set forth in claim 1, wherein the magnetic field strength threshold alarm is configured such that the sensor is responsive to a magnetic field from a nuclear magnetic resonance device.

11. The magnetic field strength threshold alarm as set forth in claim 1, wherein the magnetic field strength threshold alarm is configured to be attached to equipment that may be brought into an MRI magnet room, and which will provide an alert in response to a magnetic field from an MRI within the MRI magnet room above the predetermined threshold of the strength of the magnetic field at the location of the equipment.

12. The magnetic field strength threshold alarm as set forth in claim 1, wherein the magnetic field strength threshold alarm is configured to be worn by a person.

* * * * *